United States Patent [19]

Atsumi

[11] 4,325,371
[45] Apr. 20, 1982

[54] LOQUAT-LEAF MOXIBUSTION THERAPY AND A MOXA STICK FOR USE IN THE THERAPY

[76] Inventor: Koukichi Atsumi, No. 2592-2, Koike-cho, Hamamatsu City, Shizuoka Prefecture, Japan

[21] Appl. No.: 893,717

[22] Filed: Apr. 5, 1978

[30] Foreign Application Priority Data

Apr. 8, 1977 [JP] Japan ............................... 52-44435

[51] Int. Cl.² .................................................. A61F 7/00
[52] U.S. Cl. .................................................. 128/254
[58] Field of Search ............ 128/254, 399, 172, 24.1, 128/68.1; 424/16, 18, 40, 195

[56] References Cited

U.S. PATENT DOCUMENTS 1,235,022 7/1917 Fuji .................................... 128/254
1,817,823 8/1931 Ito ..................................... 128/254

*Primary Examiner*—Lawrence W. Trapp
*Attorney, Agent, or Firm*—Haseltine, Lake & Waters

[57] ABSTRACT

A loquat-leaf moxibustion therapy in which a green leaf of loquat and thereupon mattings of vegetable fibers such as for example the combination of a mat of cotton fabric and a mat of paper are placed preferably in this sequence on the surface of the body skin of a subject in the region of a desired "remedial spot" of the subject and thereafter a moxa stick kindled at one axial end thereof and pointed to the remedial spot across the layers of the mattings and the leaf is pressed at the fiery end of the stick onto the mattings so that the loquat leaf is locally fumigated by the smoke from the moxa stick for producing the combined medicinal effects of the moxa and the loquat leaf and, at the same time, the subject's body skin is pressed upon at the remedial spot and enjoys the remedial efficacy obtainable by the finger-pressure therapy known in the art of oriental medicine. There is further proposed a moxa stick which is sized and/or configured to be specifically suitable for use in a loquat-leaf moxibustion therapy.

30 Claims, 8 Drawing Figures

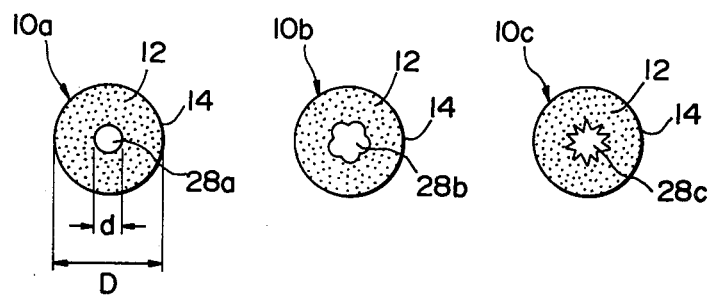
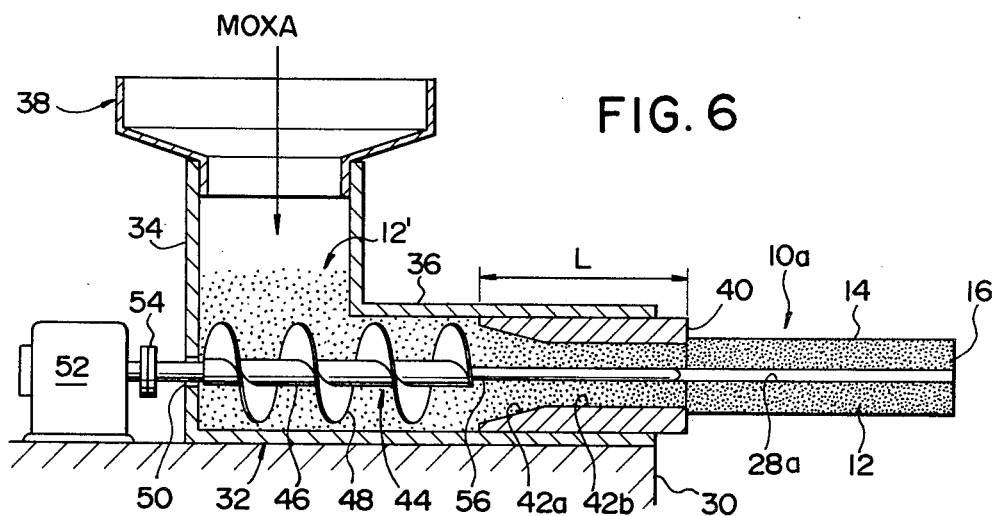

LOQUAT-LEAF MOXIBUSTION THERAPY AND A MOXA STICK FOR USE IN THE THERAPY

FIELD OF THE INVENTION

The present invention relates in general to medical treatment using medicinal plants and plant materials and, particularly, to a physiotherapeutic treatment which may fall, prima facie, under the category of moxibustion therapy. More particularly, the present invention is concerned with a loquat-leaf moxibustion therapy utilizing a leaf of loquat in combination with moxa, and further with a moxa stick which is advantageous especially when used as medicinal means in practicing the loquat-leaf moxibustion therapy. The present invention also appertains to a method of and an apparatus for manufacturing such a moxa stick on a commercial basis.

GENERAL BACKGROUND OF THE INVENTION

Of the various kinds of plants and plant materials which have been employed in medicine over the centuries, comparatively few remain in use today in limited quarters of the world. In the field of the oriental medicine, one of the few kinds of therapeutic plant materials which still occupy an important place in the modern materia medica is the moxa which is used as a celefactive counter-irritant in the moxibustion therapy or as an escharotic in the moxa cautery. The moxa to be employed in the moxibustion therapy or the moxa cautery is produced from leaves of a perennial herb of the genus Artemisia belonging to the family of sunflower or the Compositae, and consists of down, usually artificially bleached, separated from dried leaves of the herb. The most used of the Artemisia as the plant to produce moxa in the oriental moxibustion therapy or moxa cautery is the species known as *Artemisia princeps* which occurs as a natural weed or which is commercially cultivated in some limited parts of the world such as Japan and the Korean Peninsula.

For carrying out the moxibustion therapy or the moxa cautery in the simplest and perhaps most traditional fashion, a small quantity of moxa in a downy state is compacted between finger tips and is placed in a heap directly on the surface of a desired part of the subject's body skin. The heap of the moxa is then kindled at its top by the use of, for example, a thin stick of incense which is lit at one end thereof. The fire in the heap of the moxa slowly propagates toward the bottom of the heap and transfers heat to the subject's internal tissue through the skin underneath the moxa smoldering thereon. As the fire in the heap of the moxa approaches the subject's body skin, the subject will experience a sensation of heat on the skin under treatment. In the case of the moxibustion therapy, the smoldering remains of the moxa which is thus about to be burnt up on the surface of the subject's body skin are removed from the subject for thereby putting an end to one operation of the moxibustion treatment for the subject before the fire in the heap of the moxa reaches the surface of the skin. In practicing the moxa cautery, the heap of the moxa once kindled is maintained on the subject's body skin until the total quantity of the moxa applied to the skin is burnt up or the fire in the heap of the moxa reaches the surface of the skin. Thus, the moxa cautery not only destroys the tissue of the subject's body skin but also causes the subsequent formation of an eschar or scab which is ultimately replaced by a scar. Using an incense for setting fire to the moxa has no positive, technical or practical significance.

In order that the moxibustion or moxa-cautery treatment to be conducted for a subject suffering from any physical defect, lesion or ill health have a noticeable virtue as a therapeutic or remedial measure, it is of critical importance that the heap of the moxa or a quantity of moxa otherwise compacted into lump form be located correctly and accurately at a specific point or spot of the surface of the subject's body skin. Such a point or spot is well known as "tsubo" in the art of oriental medicine, particularly in the fields of the moxa cautery and the finger-pressure therapy as well as the moxibustion therapy to which the present invention appertains. While expert opinions are divided as to their exact number, there are empirically known tens to hundreds of tsubos distributed over various parts of human body. The exact location of the tsubo points or spots on persons to undergo the treatment vary subtly from one person to another and depending upon the natures of the efficacy to be obtained by the treatment or upon the natures or symptoms of the diseases or physical disorders to be cured. To enable unexperienced people to practice the therapy without aid of the directions or guidance of professional practitioners, there are published various tsubo charts or maps delineating the distribution of representative tsubo points or spots on human body. When the tsubo at which the moxibustion therapy or the moxa cautery is to be effected for a subject is properly selected and the heap of the moxa is accurately located at the particular point or spot, not only the treatment will produce its guaranteed remedial efficacy but substantially no unbearable sensation of heat is inflicted upon the subject under treatment even when the fire in the moxa is burning the skin.

There being no literary or established English translation of the original term "tsubo" in the Japanese language, the particular point or spot will be hereinafter referred to as remedial spot for convenience sake. Furthermore, the term "remedial" herein referred to in connection with the tsubo point or spot should be construed to be representative of any medically favorable effect which can be expected of or achieved by a physiotherapeutic treatment to be practiced for curative, palliative, analeptic, recuperative or prophylatic purposes. The above mentioned finger-pressure therapy is an oriental version of the chiropractic and resembles the chiropractic therapy in that both involve manipulation of human body by application of finger pressure to the subject's the internal tissues through the body skin for therapeutic purposes. The former is however distinguished from the latter in that the oriental-fashioned finger-pressure therapy extends to almost every part of the human body in contrast to the chiropractic therapy in which major adjustments are made on or in the region of the spinal column and, in some cases, in the neighborhood of the pelvis as well.

As one of the modified versions of the moxibustion therapy, there is known a loquat-leaf moxibustion therapy which uses a leaf of loquat in combination with moxa. Loquat, known also as a Japanese medler or *Eriobotrya japonica*, is a shrub of the family Malaceae and is a native of Japan and China, whence it has been taken to various subtropical climates throughout the world. In a traditional method of practicing the loquat-leaf moxibustion therapy, a green or unwithered and undried leaf of loquat is placed face down on the surface of the subject's body skin in such a manner that the loquat leaf covers a desired remedial spot of the body skin, whereupon a certain quantity of moxa is placed in heap form on the reverse or upper side of the leaf having its front face in contact with the surface of the subject's body skin. The heap of the moxa on the loquat leaf is thereafter kindled at its top so that, in a short while after the moxa is kindled, the heat produced by the smoldering moxa is transferred through the layer of the loquat leaf to the subject's body skin and stimulates the internal tissues below the skin. A calefactive counter-irritative stimulus is thus imparted to the subject's internal tissues underneath the skin around the remedial spot over which the moxa is smolding, producing a vital reaction in the internal tissues without causing a burn on the skin under treatment. The green loquat leaf intervening between the smoldering moxa and the subject's body skin is partially fumigated by the hot smoke emanating from the heap of the moxa so that the medicinal essence contained in the leaf is caused to transude from the front or lower surface of the leaf. The medicinal essence thus extravasated from the green loquat leaf acts on the dermal tissues and through the dermal tissues on the internal tissues of the subject. There are a number of reports and clinical data which have been published in corroboration of the therapeutic usefulness of the medicinal constituents of loquat leaves on the basis of the empirical evaluation of the time-tested efficacy of the loquat-leaf moxibustion therapy. The loquat-leaf moxibustion therapy is thus effective to have the intrinsic therapeutic virtue of moxa combined in effect with the medicinal properties of a green loquat leaf, thereby providing an enhanced therapeutic efficacy that could not be achieved by the ordinary moxibustion therapy using moxa alone. Since, furthermore, the heat from the moxa alight is transferred to the subject's body skin through the layer of the fresh loquat leaf, the subject under treatment is not subjected to a perceivable pain and feels only a slight sensation of warmth at the surface of the skin below the smoldering moxa. It will thus be understood that the loquat-leaf moxibustion therapy is distinguished from the moxa cautery which is a variant of the caustic therapeutics that cause local destruction of dermal and epidermal tissues by the heat generated at the surface of the subject's body skin.

To provide ease of storage and handling and to enable the operator of the therapy to accurately set the moxa at a desired remedial spot in practicing the moxibustion therapy using the moxa alone, it has been proposed and put into practice to have a quantity of moxa rolled and packed in paper into the form of an elongated, generally cylindrical stick which is similar in external appearance to a paper-rolled cigarette. When in use, the moxa stick having such a configuration is kindled at one end thereof and is applied sheer to the subject's body skin in such a manner that the lighted or business end of the stick is located at a desired remedial spot. If, in this instance, the moxa stick is forcefully pressed against the subject's body skin, not only the heat produced at the business end of the stick is transferred to the subject as in the ordinary moxibustion therapy but a physical pressure is imparted to the remedial spot at which the moxa stick is being pressed shear onto the skin as in the previously mentioned finger-pressure therapy. A moxa stick used in this fashion is thus capable of providing the curative effects of the finger-pressure therapy in addition to the effects which can be ordinarily achieved by the moxibustion therapy. The present invention contemplates combining the medicinal efficacy of an ordinary moxibustion therapy with not only the curative effects of the finger-pressure therapy but the therapeutic virtue which can be obtained by the leaves of loquat as medicinal agents.

It is, accordingly, an important object of the present invention to provide an improved loquat-leaf moxibustion therapy in which the moxa packed in the form of a stick or rod is utilized in combination with a green leaf of loquat and in which the moxa stick is applied under pressure to the subject's body across the layer of the loquat leaf placed on the surface of the body skin in such a manner as to cover a remedial spot under the leaf.

For the purpose that the loquat-leaf moxibustion therapy using a moxa stick displays satisfactory physiotherapeutic effects of the finger-pressure therapy, it is important that the pressure applied from the moxa stick to the subject's body under treatment be concentrated at a selected remedial spot of the subject as efficiently as possible. From this point of view, it is desired that a moxa stick for use in the loquat-leaf moxibustion therapy according to the present invention be as slender or small in diameter as possible so as to limit the area of the subject's body skin to be subjected to the pressure from the moxa stick which is forced against the subject's body by the operator of the therapy during treatment.

When a loquat leaf is placed on the surface of the body skin of a subject about to undergo a loquat-leaf moxibustion therapy and the loquat leaf is located to cover a desired remedial spot of the subject's body, the remedial spot is concealed from the view of the operator of the therapy with the result that the operator is not permitted to visually probe and determine the exact location of the remedial spot at which the moxa stick is to be pointed. From this point of view, it is advantageous that a moxa stick for use in the loquat-leaf moxibustion therapy according to the present invention be as stick or large in diameter as possible so as to be capable of covering as large an area of the subject's body skin as possible at its fiery business end.

When a moxa stick is in use, furthermore, the moxa stick is gradually exhausted in a tapered form away from the initially kindled end of the stick. As the moxa stick is exhausted and shortened, there are produced smoldering remains of moxa at the tapered fiery end of the stick. If the treatment using the moxa stick is continued on the subject with such smoldering remains of moxa left attached to the stick, the tapered, exhausted tip portion of the moxa stick tends to break into crumbles and then into ashes. Such a tendency becomes pronounced as the moxa stick to be put to use is made slenderer and accordingly more apt to be tapered toward the end. The crumbles and ashes may cause the operator of the therapy to burn his finger or palm gripping the moxa stick or, down the moxa stick and the subject's body, may singe or burn the subject's or operator's clothes, the surface of the floor or carpet, or the bed-clothes, if any. To preclude these dangers, the moxa stick which has been exhausted and tapered to such an extent that the tapered fiery tip portion of the stick appears to be on the point of being crumbled may be once removed from the subject in the course of the treatment, so as to sever the fiery tip portion from the remaining portion of the moxa stick by the use of a knife or scissors before the tip portion is broken into crumbles. If this is done before the treatment is complete, the moxa stick to be put to continued use must be kindled at the cut end and applied for a second time to the subject for proceeding with the treatment. These procedures will not only create a problem that the therapeutic treatment must be interrupted for the removal of the exhausted tip portion from the moxa stick and the relighting of the stick to be put to further use but will result in a waste of moxa because of the fact that a considerable amount of raw moxa must be discarded together with the exhausted remains to be removed from the moxa stick. All these inconveniences could be alleviated if the moxa stick has a sufficiently robust construction which will make the moxa stick substantially free from the tendency of being exhausted in a tapered form when in use. From this point of view, it is also desired that a moxa stick to be utilized for practicing the loquat-leaf moxibustion therapy according to the present invention be as thick or large in diameter as possible. This requirement is apparently contrary to the previously described requirement that a moxa stick for use in the loquat-leaf moxibustion therapy according to the present invention should be as slender or small in diameter as possible. Thus, the present invention further contemplates provision of a moxa stick which will provide a reasonable compromise between the mutually conflicting requirements of a moxa stick to be used in the loquat-leaf moxibustion therapy provided by the present invention.

It is, accordingly, another important object of the present invention to provide a moxa stick which is sized to be optimum for achieving proper medicinal virtues of the conventional loquat-leaf moxibustion therapy and physiotherapeutic effects tantamount to the curative effects of the finger-pressure therapy.

It is still another important object of the present invention to provide a moxa stick which is thick or large in diameter enough to minimize the tapering and accordingly crumbling tendency of an exhausted tip portion of the stick and to enable the user of the moxa stick to easily and accurately apply the stick to a desired remedial spot below the loquat leaf placed on the subject's body skin and which is nevertheless slender or small in diameter enough to be capable of applying a concentrated pressure or thrust to the remedial spot when the moxa stick is pressed against the subject's body under treatment.

Yet, it is another important object of the present invention to provide an improved moxa stick which is so configured or preferably so configured and dimensioned in cross section as to preclude the moxa stick from forming a tapered tip portion when the moxa stick is being exhausted and shortened away from its end alight during prosecution of a loquat-leaf moxibustion therapy using the moxa stick.

It is still another object of the present invention to provide a method of manufacturing such an improved moxa stick on a commercial basis. A further object of the invention is to provide an apparatus adapted to put the method into practice at a low cost.

SUMMARY OF THE INVENTION

In accordance with one outstanding aspect of the present invention, there is provided a loquat-leaf moxibustion therapy comprising setting on the surface of the subject's body skin layers of a loquat leaf placed face down on the surface of the skin and located to cover a selected remedial spot of the subject's body and mattings of vegetable fibers placed on the loquat leaf, applying a moxa stick kindled at one axial end thereof onto the mattings in such a manner that the kindled end of the moxa stick is axially directed to the remedial spot across the layers of the mattings and the loquat leaf, and pressing the moxa stick axially onto the mattings for causing the moxa stick to axially thrust at its kindled end against the subject's body in the region of the remedial spot across the layers of the mattings and the loquat leaf.

It is to be noted that the "body" herein referred to as in connection with the subject's body or subject's body skin is not limited to the truncal part of human body but extends to the limbs and the cervical region of the human body.

In accordance with another outstanding aspect of the present invention, there is provided a moxa stick for use in a loquat-leaf moxibustion therapy, comprising an elongated mass of moxa having a substantially circular cross section measuring within the range between about 22 millimeters and about 24 millimeters in diameter substantially throughout the length of the mass of the moxa. As an alternative, a moxa stick according to the present invention may comprise an elongated mass of moxa formed with a bore throughout the length of the mass of the moxa.

BRIEF DESCRIPTION OF THE DRAWINGS

The features and advantages of a loquat-leaf moxibustion therapy according to the present invention and those of a moxa stick for use in the therapy in accordance with the present invention will be understood more clearly from the following description taken in conjunction with the accompanying drawings, in which:

FIGS. 5A, 5B and 5C are cross sectional views showing the respective cross sections of preferred embodiments of an improved moxa stick provided by the present invention; and FIG. 6 is a vertical or longitudinal elevational view of an apparatus adapted to manufacture a moxa stick having a cross section illustrated in FIG. 5A.

DETAILED DESCRIPTION OF THE INVENTION

Figure 1:
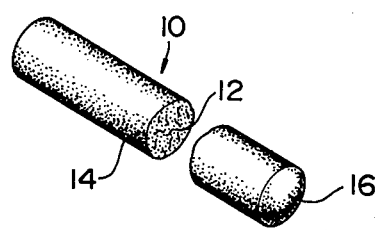
FIG. 1 is a fragmentary perspective view showing a moxa stick which may be used for practicing a loquat-leaf moxibustion therapy according to the present invention.

Referring to the drawings, first to FIG. 1, a moxa stick 10 for use in a loquat-leaf moxibustion therapy according to the present invention comprises a mass of moxa 12 which is compacted and wrapped in a generally cylindrical or tubular receptacle or wrapper 14. The moxa 12 consists of down separated from leaves of a species, preferably *Artemisia princeps*, selected from the genus Artemisia. The receptacle or wrapper 14 for the moxa 12 is formed of paper, preferably Japanese-fashioned hand-made paper prepared from the pulp of Broussonetia (paper mulberry) or *Bitulaceae papyrifera*

(white canoe, or paper, birch). The receptacle or wrapper 14 is shown having at one axial end thereof an end seal 16 covering the mass of the moxa 12 at one end of the moxa stick 10. At the other end of the moxa stick 10, the receptacle or wrapper 14 may also have an end seal covering the mass of the moxa 12 at the other axial end of the receptacle or wrapper 14 or may be open for having the mass of the moxa 12 exposed at the opposite end of the stick 10 to the end seal 16, though not shown in the drawings.

Figure 2:
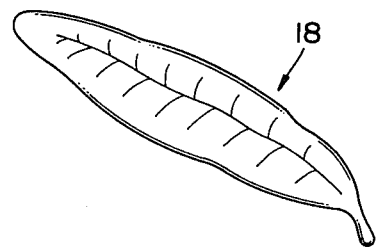
FIG. 2 is a perspective view showing a loquat leaf for use with a moxa stick in loquat-leaf moxibustion therapy.

Turning to FIG. 2 of the drawings, a leaf of loquat as indicated at 18 is a relatively thick, simple and entire evergreen leaf which is rather broad in outline and minutely indented along its margin and which has pinnate veins, the indentations of the margin being not illustrated in the drawing. The inventor's clinical experiences have revealed that excellent results are achieved when a loquat leaf used in a loquat-leaf moxibustion therapy is rather aged and deep-colored.

Figure 3:
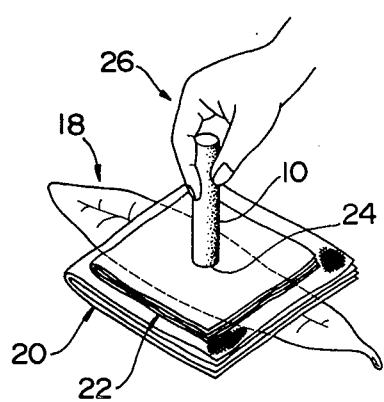
FIG. 3 is a perspective view showing a step of the loquat leaf moxibustion therapy using the moxa stick and loquat leaf shown in FIGS. 1 and 2.

For practicing the loquat-leaf moxibustion therapy according to the present invention, the loquat leaf 18 is first placed face down on the surface of the body skin of a subject in such a manner that the leaf covers thereunder a selected remedial spot of the subject's body. On the loquat leaf 18 thus lying on the subject's body skin with its reverse side directed upwardly are further placed a lower mat 20 of suitable textile fabric and an upper mat 22 of paper mounted atop the lower mat 20 as shown in FIG. 3. The textile fabric forming the lower mat 20 is preferably a bleached cotton fabric and the paper forming the upper mat 22 is preferably a Japanese-fashioned hand-made paper prepared from the pulp of white canoe birch or paper mulberry similarly to the paper forming the receptacle or wrapper 14 of the moxa stick 10. By preference, each of the textile fabric and the paper forming the mats 20 and 22 may be folded into a suitable number of substantially coextensive or otherwise overlapping layers or sections overlying one another. In the arrangement illustrated in FIG. 3, each of the textile fabric forming the lower mat 20 and the paper forming the upper mat 22 is assumed to be folded three times to form eight substantially coextensive layers overlying one another. The lower and upper mats 20 and 22 thus constitute mattings of vegetable fibers on top of the loquat leaf 18. To set such mattings on the loquat leaf, the mats 20 and 22 may be placed either in a single unit on the loquat leaf 18 or sequentially in such a manner that the lower mat 20 is first placed on the loquat leaf 18 and thereafter the upper mat 22 is placed on top of the lower mat 20. If desired, the loquat-leaf 18 and the mats 20 and 22 may be assembled together separately of the subject's body for being mounted all in a single unit on the subject's body skin.

The preparations are complete for commencing the treatment for the subject when fire is set to the moxa stick 10. If, in this instance, the moxa stick 10 has the end seal 16 only at one end thereof, the moxa stick should be kindled at its end having the moxa exposed. If the moxa stick has the end seals at both ends thereof, one of the end seals should be removed from the stick so that the moxa stick can be kindled at the end from which the end seal has been removed. The moxa stick 10 thus kindled at one end as indicated at 24 in FIG. 3 is applied to the mattings by hand 26 in such a manner that the kindled end 24 of the moxa stick 10 is axially directed to the subject's remedial spot across the layers of the loquat leaf 18 and the mattings composed of the lower and upper mats 20 and 22. The moxa stick 10 is axially pressed onto the mattings so as to axially thrust at the kindled end 24 against the subject's body at or in the region of the remedial spot across the layers of the mattings and the loquat leaf 18. In a short while after the moxa stick 10 alight is thus applied to the subject, heat produced by the smoldering of the moxa 12 in the moxa stick 10 is transferred through the layers of the mats 22 and 20 and the loquat leaf 18 to the subject's body skin and through the skin to the subject's internal tissues below the remedial spot. A calefactive counter-irritative stimulus is thus imparted to the subject's internal tissues underneath the remedial spot of the skin and brings about a vital reaction in the internal tissues without causing a burn on the subject's body skin. The heat produced in the moxa stick 10 is such that a few upper layers of the upper mat 22 of paper are slightly scorched immediately below the fiery or business end of the moxa stick 10. Thus, the lower mat 20 of the textile fabric underneath the paper mat 20 remains substantially intact although the former as well as the latter is subjected to the attack of the hot smoke emanating from the smoldering moxa stick 10. The hot smoke issuing from the moxa stick 10 is passed through the paper mat 22 and further through the mat 20 of the textile fabric to the upper reverse side of the loquat leaf 18. The green loquat leaf 18 in this fashion fumigated by the smoke produced by the combustion of the moxa 12 in the moxa stick 10 with the result that the medicinal essence contained in the leaf 18 is caused to transude from the lower from surface of the leaf. The medicinal essence thus extravasated from the green loquat leaf 18 acts on the dermal tissues and through the dermal tissues on the internal tissues of the subject under treatment, thereby exercising medicinal therapeutic effects over the subject's internal tissues below the remedial spot. The treatment is continued until the subject complains of a slight sensation of warmth at the surface of the skin under treatment. When the subject feels such a sensation, the moxa stick 10 is removed from the subject and, if it is desired to put an end to the remedial spot for the remedial spot at this stage, the loquat leaf 18 and the mats 20 and 22 may also be removed from the subject. If, however, it is desired to further proceed with the treatment for the subject at the same treatment, the loquat leaf 18 may be slightly displaced from the original position on the subject's body skin so that the affected portion of the leaf is dislodged from the remedial spot and instead of a fresh or unaffected portion of the leaf is located above the remedial spot for which the treatment is to be continued. The moxa stick 10 is for a second time applied and pressed onto the subject's body so as to proceed with the treatment as before.

Figure 4:
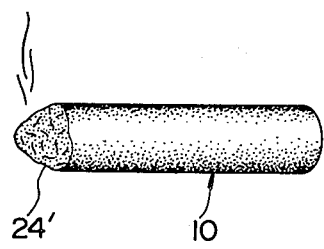
FIG. 4 is a side view showing a moxa stick which is partially exhausted to form a tapered fiery end portion during use of the stick in the loquat-leaf moxibustion therapy according to the present invention.

While the moxa stick 10 which is alight at one end is being applied to the subject across the layers of the mats 20 and 22 and the loquat leaf 18, the moxa stick is gradually exhausted and shortened away from the initially kindled end thereof, as is observed with a cigarette being smoked. As the moxa stick 10 is thus exhausted and shortened during prosecution of the therapy, the fiery tip portion of the moxa stick 10 becomes tapered toward the extreme end of the portion as indicated at 24' in FIG. 4 and tends to break into crumbles and ashes if the treatment with use of the moxa stick 10 is continued with the smoldering remains of the moxa left attached to the stick. The tapered fiery tip portion 24' of the moxa stick 10 must therefore be severed from the remaining portion of the stick before such a portion is crumbled off the stick in the process of the treatment.

Not only extra time-consuming steps are thus required for the removal of the tapered fiery tip portion 24' from the moxa stick 10 and probably further for the relighting of the stick to be put to continued use but a considerable amount of raw moxa must be discarded together with the exhausted tip portion to be removed from the moxa stick, inviting a waste of moxa as previously pointed out. Experiments conducted by the inventor have revealed that the quantity of the moxa that must be wasted for this reason amounts to approximately five percent of the total quantity of the moxa that would be available by one moxa stick were it not for such a loss of the moxa. The quantity of the moxa that would be available by a moxa stick without any loss of moxa substantially equals the total quantity of the moxa initially contained in the moxa because of the fact that a moxa stick can be and is usually used up from end to end.

The quantity of the moxa which must be discarded for the above described reason can be reduced if the crumbling and accordingly tapering tendency of the moxa stick is alleviated. Such a tendency of a moxa stick in turn can be lessened if the moxa stick is enlarged in diameter so as to have a robust construction, as previously discussed. Increasing the diametral measurement of a moxa stick is further conducive to the purpose of enabling the user of the moxa stick to easily and accurately apply the stick to a desired remedial spot of the subject's body during treatment, as has also been discussed. If, however, the diametral measurement of a moxa stick is made larger, the pressure which is to be transferred to the subject's body from the moxa stick being pressed by the operator of the therapy is distributed over the larger area. Extensive experiments with moxa sticks having different diameters have therefore been conducted by the inventor in quest of an optimum range of the diametral measurement of moxa sticks for use in the loquat-leaf moxibustion therapy according to the present invention. These experiments have proved that such a range is between about 22 millimeters and about 24 millimeters. If moxa sticks having diameters larger than this range and thus falling within the range of, for example, between 25 millimeters and 28 millimeters are employed for practicing the therapy, the operator of the therapy is practically ensured from missing the selected remedial spot in pointing at the spot with the moxa stick across the loquat leaf and the mattings thereon but the pressure transferred from the moxa stick to the subject's body is broadly distributed around the remedial spot so that physiotherapeutic effects of the finger-pressure therapy can not be achieved satisfactorily. It is also pointed out by the users of such thick moxa sticks that the sticks are cumbersome to handle and manipulate. If, conversely, moxa sticks haveing diameters less than the range of about 22 to 24 millimeters and thus falling within the range of, for example, between 15 millimeters and 20 millimeters are used in the loquat-leaf moxibustion therapy according to the present invention, then the tapering and crumbling tendency of the moxa stick become critically pronounced and, in addition, the operator of the therapy becomes liable to miss the target remedial spot frequently, although a sufficiently concentrated pressure can be applied from the moxa stick to the remedial spot of the subject. It may also be noted that a number of subjects who have been treated with such slender moxa sticks complain that they have had unsatisfied feelings during and after the treatment. As a matter of fact, the clinical experiences of the inventor tell that the remedial efficacy obtained by effecting the therapy with use of these slender moxa sticks is actually quite unsatisfactory.

Further experiments have been conducted by the inventor in an effort to evaluate the usefulness of moxa sticks having different diametral measurements falling within the preferred range specified above. The results of these experiments show that, while the tapering and crumbling tendency of a moxa stick can be advantageously reduced when the moxa stick has a diametral measurement within such a range, the particular tendency can not be completely eliminated insofar as the moxa stick is solid in its entirety. Thus, the present invention proposes to have a moxa stick formed with an axial bore throughout the length of the elongated mass of the moxa forming the stick. The moxa stick having such a bore may be sized and configured as desired in overall cross section but, for the purpose of exploiting the advantages achivable by the formation of the bore, it is preferable that the moxa stick formed with the axial bore have a diametral measurement within the above specified range of between about 22 millimeters and about 24 millimeters.

FIGS. 5A, 5B and 5C show the cross sectional configurations of moxa sticks 10a, 10b and 10c, respectively, each of which is thus formed with an axial bore in and throughout the length of the elongated mass of the moxa 12. The moxa stick 10a illustrated in FIG. 5A is formed with an axial bore 28a having a substantially circular cross section which is substantially concentric to the circular cross section of the stick 10a as a whole, viz., having a center axis which is substantially coincident with the center axis of the stick. Turning to FIG. 5B, the moxa stick 10b is shown formed with an axial bore 28b having a multi-curved or multi-lobed, generally circular cross section with a center axis substantially coincident with the center axis of the stick 10b as a whole. The lobes of the cross section of the bore 28b are shown to be five in number and arranged substantially regularly about the center axis of the bore but, if desired, may be arranged irregularly about the axis and provided in any desired number other than five. On the other hand, the moxa stick 10c shown in FIG. 5C is formed with an axial bore 10c having an echino-stelliform or denticularly stelliform cross section also having a center axis substantially coincident with the center axis of the stick 10c. The number and the individual shapes of the radial prickles of the cross section as shown in FIG. 5C are not limitative of the generally stelliform cross section of the axial bore 28c. Furthermore, these prickles are shown to be irregularly arranged about the center axis of the cross section of the bore 28c but may be arranged substantially regularly about the axis.

When a moxa stick thus formed with an axial bore throughout the length of the mass of the moxa is kindled at one end thereof and exhausted away from the end alight, the moxa stick can not be tapered toward the fiery end in the absence of a central part in the cross section of the stick. The moxa stick is therefore exhausted substantially uniformly away from the initially kindled end thereof and constantly forms a substantially even end face at the business end irrespectively of the diametral measurement of the stick. This has been ascertained by various tests and experiments conducted on a clinical basis.

As a result of the formation of an axial bore in a moxa stick, there is invited a reduction in the packing percentage of the moxa in the stick if the packing density of the moxa is unchanged. The "packing percentage" herein referred to is defined as the percentage of the quantity by weight of the moxa actually contained in a given moxa stick and the quantity by weight of the moxa which could be contained in the moxa stick if the moxa stick is solid in its entirely, viz., in the absence of an axial bore in the stick as in an ordinary moxa stick. The reduction in the packing percentage of a moxa stick results in a reduction in the total period of time for which the combustion of the moxa stick lasts, viz., the moxa stick is operable for a therapeutic treatment using the moxa stick.

As previously noted, the loss of raw moxa as inevitably invited in a solid moxa stick for the removal of an exhausted tip from the stick in use usually amounts to approximately five percent of the total quantity of the moxa originally contained in the moxa stick. If, therefore, the decrement in the packing percentage of a moxa stick having an axial bore is approximately equal to or less than five percent, then the resultant decrement in the time duration for which the moxa stick is operable for the therspeutic treatment of a subject can be deemed practically negligible or may be acceptable for practical purposes when compared with the decrement to be invited in such a duration as a result of the loss of the raw moxa in a solid moxa stick. When, furthermore, the moxa in a moxa stick is compacted in a void-free fashion to a certain density which is substantially uniform throughout the resultant mass of the moxa, the quantity by weight of the moxa forming the mass is largely proportional to the volume of the mass.

For these reasons, it is preferable that the axial bore formed in a moxa stick provided by the present invention be so sized as to have a volume up to about five percent of the external volume of the mass of the moxa forming the stick. If, therefore, the cylindrical mass of the moxa of the bored moxa stick 10a illustrated in FIG. 5A is substantially uniform in cross section throughout the length of the stick and has an outside diameter D and an inside diameter d (which is also the diameter of the axial bore 28a in the stick), it is preferable that there hold the relation $D^2 \geq 20d^2$, hence approximately $d \leq D/4.47$ between the diameters D and d. Considering that the thickness of the receptacle or wrapper 14 formed of paper is practically engligible, this relation is substantially satisfied when the diameter d of the bore 28a in the stick 10a is less than about 5 millimeters. For other reasons, especially for the purpose of providing ease in fabricating a moxa stick having an axial bore in a compacted mass of initially downy moxa and for the purpose that the compacted mass of the moxa in a moxa stick thus produced is capable of maintaining its initial internal configuration and accordingly packing density throughout the periods of time for the transportation, storage and use of the stick, it is further preferred that the diameter d of the axial 28a in the moxa stick 10a shown in FIG. 5A be greater than about 2 millimeters.

When, thus, a moxa stick provided by the present invention has a generally cylindrical external configuration having an outside diameter within the range of between about 22 and 24 mm and is formed with an axial bore having a substantially circular cross section which is substantially iniform throughout the length of the stick, it is preferable that the diameter of the axial bore, viz., the inside diameter of the moxa stick be within the range of about 2 millimeters and about 5 millimeters. If, therefore, the moxa stick 10a shown in FIG. 5A is so sized that the outside diameter D of the stick is about 22 mm. viz., selected at the lower limit of the preferred range of the diameter D and that the diameter d of the axial bore 28a in the stick is within the preferred range of between about 2 and 5 mm, then the decrement in the packing percentage of the moxa 12 in the stick as caused by the formation of the axial bore 28a falls within the range of between about 0.8% and about 5.2%. If, on the other hand, the moxa stick 10a is sized so that the outside diameter D of the stick is about 24 mm, viz., selected at the upper limit of the preferred range of the diameter D and that the diameter d of the bore 28a is within the range of from about 2 to about 5 mm, then the decrement in the packing percentage of the moxa as caused by the formation of the bore 28a falls within the range of between about 0.7% and about 4.3%. These mean that, when a moxa stick having the configuration illustrated in FIG. 5A has an outside diameter within the range of between about 22 millimeters and about 24 millimeters and the axial bore formed in the stick has a diameter within the range of between about 2 millimeters and about 5 millimeters as above specified, the decrement in the packing percentage of the moxa in the stick as caused by the formation of the bore ranges from about 0.7% to about 5.2% and is thus approximately equal to or even smaller than the decrement as caused in an ordinary solid moxa stick in which a certain amount of raw moxa must be wasted for removing an exhausted tip portion of the stick during use of the stick.

When a moxa stick formed with an axial bore is in use for practicing the loquat-leaf moxibustion therapy according to the present invention and is thus pressed at its fiery business end onto the mattings lying on a loquat leaf placed on the surface of the body skin of a subject, the smoke produced by the combustion and smoldering of the moxa at the business end of the stick is confined in the bore closed by the end seal at the opposite end of the stick to the business end and develops a pressure in the bore as the treatment using the stick proceeds. The pressure of the smoke acts on the loquat leaf through the mattings over the leaf and further on the subject's body through the loquat leaf underneath the mattings and aids in permeation of the smoke into the cellular tissue of the leaf, thereby promoting the fumigation of the leaf with the smoke emanating from the moxa stick. Thus, the moxa stick is capable of being effective throughout its cross sectional area at the fiery end of the stock although the stick is void of moxa over a central portion of the area. It may also be noted that fire can be set more easily to a moxa stick having an axial bore than to an ordinary solid moxa stick because the former can be kindled only along its annular foremost end while the latter must be lit over its front end area in the absence of an opening in the area.

FIG. 6 shows a preferred example of an apparatus adapted to manufacture bored moxa sticks having cross sections similar to the cross section illustrated in FIG. 5A. The apparatus is shown to be installed on a suitable stationary support 30 and to comprise a hollow body structure 32 fixedly mounted on the support 30. The body structure 32 comprises a vertical column portion 34 which is open at its upper end and a horizontal cylinder portion 36 extending horizontally from a lower part of the column portion 32 and open at its rearmost end opposite to the column portion. A generally funnel-shaped hopper 38 is closely fitted at its lower end to the open upper end of the vertical column portion 34 for permitting entry of moxa into the body structure 32 through the hopper 38 as indicated by an arrow. The moxa thus admitted down into the body structure 32 through the hopper 36 is first accumulated in a lower portion of the internal space in the column portion 34 as indicated at 12' in the drawing. A generally cylindrical extrusion die member 40 is closely but detachably fitted to and received in the cylinder portion 36 and axially extends into the cylinder portion 36 in such a manner that the inner axial end of the die member is located at a predetermined distance from the lower portion of the internal space in the vertical column portion 34 of the body structure 32. The extrusion die member 40 is formed with an axial bore which consists of a frusto-conical or counter-tapered inner axial bore portion 42a flaring toward and terminating at the inner axial end of the die member and a cylindrical outer axial bore portion 42b merging out of the counter-tapered bore portion 42a and open at the outer axial end of the die member, the bore portions 42a and 42b having respective center axes which are substantially in line with each other and preferably further with the center axis of the cylinder portion 36 of the body structure 32. The cylindrical outer bore portion 42b in the die member 40 has a diameter which is slightly smaller than the desired outside diameter of the cylindrical mass of the moxa to form a moxa stick to be manufactured for the reason to be explained later.

The apparatus shown in FIG. 6 further comprises a motor-driven screw conveyor 44 comprising an elongated screw shaft 46 horizontally extending throughout the lower portion of the internal space in the vertical column portion 34 and partially into the internal space in the horizontal cylinder portion 36 of the body structure 32. The shaft 46 has an axis substantially in line with the aligned axes of the bore portions 42a and 42b in the extrusion die member 40 and terminates immediately ahead of the inner axial end of the die member 40 as shown. The conveyor assembly 44 further comprises a helical screw blade 48 which is rigidly mounted on the screw shaft 46 and which is arranged in such a manner that the moxa 12' accumulated within the vertical column portion 34 of the body structure 32 is gradually propelled toward the inner axial end of the extrusion die member 40 and further into the counter-tapered bore portion 42a in the die member 40 when the screw blade 48 is caused to rotate with the shaft 46 in one direction about the axis of the shaft 46. The screw shaft 46 thus carrying the screw blade 48 thereon is axially passed through an opening 50 formed in the vertical column portion 34 of the body structure 32 and axially projects out of the body structure 32 for connection to the output shaft of an electric motor 52 through coupling flanges 54. The screw shaft 46 is connected at its axial end adjacent to the inner axial end of the extrusion die member 40 to an elongated rod 56 which axially extends substantially throughout the bore portions 42a and 42b in the extrusion die 40 for terminating slightly short of the outer axial end of the cylindrical bore portion 42b and which has an axis which is substantially coincident in part with the center axis of the counter-tapered bore portion 42a and in part with the center axis of the cylindrical bore portion 42b. The elongated rod 56 has a circular cross section which is substantially equal to or preferably slightly larger than the desired diameter of the axial bore to be formed in a moxa stick to be manufactured for the reason which will be also explained later. The rod 56 is preferably detachably attached to the screw shaft 44.

During operation of the apparatus thus constructed and arranged, a cylindrical receptacle or wrapper 14 of paper having an end seal 16 at one end thereof is attached to the outer end face of the extrusion die member 40 in such a manner that the receptacle or wrapper 14 is open at the other end thereof to the cylindrical outer axial bore portion 42b in the extrusion die member 40 and that the center axis of the receptacle or wrapper 14 is substantially aligned with the center axis of the bore portion 42b. The receptacle or wrapper 14 is held in this position either manually or by suitable retaining means (not shown) provided in combination with or forming part of the apparatus herein shown. As the screw conveyor assembly 44 is driven to rotate about the axis of the screw shaft 46 by the motor 52, the moxa 12' accumulated within the body structure 32 of the apparatus is agitated by the screw blade 36 and if forced to gradually move away from the lower portion of the space in the vertical column portion 34 of the body structure 32 toward the extrusion die member 40 through the inner axial end portion of the space in the horizontal cylinder portion 36 of the body structure. The moxa 12' is thus forced into the axial bore in the extrusion die member 40 in which the moxa is first passed through the forwardly reduced counter-tapered bore portion 42a and is progressively compacted as the moxa is propelled to advance toward the cylindrical bore portion 42b in the die member 40. The moxa 12' is further passed through the cylindrical bore portion 42b is compacted to a certain density when the moxa is leaving the bore portion 42b in the die member 40. While the moxa 12' is being conveyed forwardly in the bore portions 42a and 42b in the extrusion die member 40, the elongated rod 56 projecting axially from the foremost end of the screw shaft 44 into the bore portions 42a and 42b is driven by the screw shaft 44 to rotate about its axis so that the moxa 12' advancing toward the foremost end of the extrusion die member 40 is compacted around the rod 56 and forms an axial bore in the compacted moxa in the cylindrical bore portion 42b in the die member 40. The moxa is therefore extruded in the form of a cylindrical mass having an axial bore from the foremost end of the extrusion die member 40 and is admitted into the receptacle or wrapper 14 attached at its open end to the outer end face of the die member 40. When the foremost end of the cylindrical mass of the moxa reaches the inner face of the end seal 16 of the receptacle or wrapper 14, the receptacle or wrapper is axially forced away from the extrusion die member 40. The receptacle or wrapper 14 is now full of the compacted mass of moxa throughout the length thereof and thus forms part of a moxa stick 10a having an elongated mass of moxa 12 packed in the receptacle or wrapper 14 and having an axial bore 28a extending throughout the length of the mass as seen in FIG. 6. The moxa stick 10a thus produced is detached from the extrusion die member 40 by cutting the mass of the moxa 12 from the mass of the moxa 12' being successively withdrawn from the die member 40. To the cut end of the mass of the moxa 12 thus separated from the extrusion die member 40 and forming the moxa stick 10a may be applied an end seal (not shown) which may be preliminarily provided as part of or separately from the receptacle or wrapper 14.

When the compacted mass of the moxa 12 is admitted from the extrusion die 40 into the receptacle or wrapper 14, the mass is allowed to slightly expand in cross section so that the mass of the moxa 12 packed in the receptacle or wrapper 14 is slightly larger in diameter than the compacted mass of the moxa 12' in the extrusion die member 40. When the mass of the moxa is thus allowed to expand in the receptacle or wrapper 14, the axial bore initially formed in the compacted mass of the moxa 12' in the extrusion die member 40 is also slightly reduced in cross section so that the axial bore 28a formed in the mass of the moxa 12 in the receptacle or wrapper 14 is slightly smaller in diameter than the axial bore initially formed in the mass of the moxa 12' in the die member 40. The diameter of the cylindrical bore portion 42b in the extrusion die member 40 being selected to be slightly smaller than the desired outside diameter of the mass of the moxa 12 to be finally formed in the receptacle or wrapper 14 and the diameter of the elongated rod 56 being selected to be slightly larger than the desired diameter of the axial bore 28a to be finally formed in the mass of the moxa 12 as previously noted, the mass of the moxa 12 admitted into the receptacle or wrapper 14 has the desired outside and inside diameters upon expansion therein.

The moxa forming a moxa stick according to the present invention is preferably prepared from the down separated from leaves of *Artemisia princeps* as previously noted. In those districts in which *Armitesia princeps* is not naturally distributed or artificially cultivated, or where moxa prepared from *Artemisia princeps* is not available, other suitable species of the genus *Artemisia*, such as sagebrush or *Artemisia tridendata* abundant in the western United States and wormwood or *Artemisia obsinthium* occurring typically in the nothern United States and Canada, may be utilized as alternatives of *Artemisia princeps*.

What is claimed is:

1. A loquat-leaf moxibustion therapy comprising setting on the surface of the subject's body skin layers of a loquat leaf placed face down on the surface of the skin and located to cover a selected remedial spot of the subject's body and mattings of vegetable fibers placed on the loquat leaf, applying a moxa stick kindled at one axial end thereof onto said mattings in such a manner that the kindled end of the moxa stick is axially directed to said remedial spot across the layers of the mattings and the loquat leaf, and pressing the moxa stick axially onto the mattings for causing the moxa stick to axially thrust at its kindled end against the subject's body in the region of the remedial spot across the layers of the mattings and the loquat leaf.

2. A loquat-leaf moxibustion therapy as set forth in claim 1, in which said mattings comprise a mat of textile fabric placed at least in part on said loquat leaf and a mat of paper placed at least in part on said mat of textile fabric.

3. A loquat-leaf moxibustion therapy as set forth in claim 2, in which said mat of paper is formed of paper prepared from the pulp of Broussonetia or *Bitulaceae papirifera*.

4. A loquat-leaf moxibustion therapy as set forth in claim 2 or 3, in which said mat of textile fabric is formed of woven cotton fabric.

5. A loquat-leaf moxibustion therapy as set forth in claim 3, in which said mat of textile fabric is formed of woven cottom fabric.

6. A moxa stick for use in a loquat-leaf moxibustion therapy, comprising an elongated mass of moxa formed with an axial bore extending throughout the length of the mass.

7. A moxa stick as set forth in claim 6, in which said mass of the moxa has a generally circular cross section throughout the length of the mass.

8. A moxa stick as set forth in claim 7, in which said mass of the moxa has an outside diameter within the range of between about 22 millimeters and about 24 in diameter throughout the length of the mass.

9. A moxa stick as set forth in claim 8, in which said axial bore has a generally circular cross section.

10. A moxa stick as set forth in claim 9, in which said axial bore has a diameter within the range of between about 2 millimeters and about 5 millimeters throughout the length of said mass of the moxa.

11. A moxa stick as set forth in claim 10 in which said moxa consists of down separated from leaves of a species selected from the genus Artemisia.

12. A moxa stick as set forth in claim 9 in which said moxa consists of down separated from leaves of a species selected from the genus Artemisia.

13. A moxa stick as set forth in claim 8, in which said axial bore has a multi-lobed, generally circular cross section throughout the length of said mass of the moxa.

14. A moxa stick as set forth in claim 13 in which said moxa consists of down separated from leaves of a species selected from the genus Artemisia.

15. A moxa stick as set forth in claim 8, in which said axial bore has a generally stelliform cross section throughout the length of said mass of the moxa.

16. A moxa stick as set forth in claim 15 in which said moxa consists of down separated from leaves of a species selected from the genus Artemisia.

17. A moxa stick as set forth in claim 8 in which said moxa consists of down separated from leaves of a species selected from the genus Artemisia.

18. A moxa stick as set forth in claim 7 in which said moxa consists of down separated from leaves of a species selected from the genus Artemisia.

19. A moxa stick as set forth in claim 6, in which said axial bore has a volume up to about 5 percent of the external volume of said mass of the moxa.

20. A moxa stick as set forth in claim 19 in which said moxa consists of down separated from leaves of a species selected from the genus Artemisia.

21. A moxa stick as set forth in claim 6, further comprising a receptacle of paper wrapping said mass of the moxa throughout the length of the mass.

22. A moxa stick as set forth in claim 21, in which said receptacle includes an end seal portion covering the mass of the moxa at one axial end of the mass and closing said axial bore at said axial end.

23. A moxa stick as set forth in claim 22 in which said moxa consists of down separated from leaves of a species selected from the genus Artemisia.

24. A moxa stick as set forth in claim 21, in which said receptacle includes two end seal portions each covering the mass of the moxa at each axial end of the mass and closing said axial bore at each axial end of the mass.

25. A moxa stick as set forth in claim 24 in which said moxa consists of down separated from leaves of a species selected from the genus Artemisia.

26. A moxa stick as set forth in claim 21, in which said receptacle is formed of paper prepared from the pulp of Broussonetiae or *Bitulaceae papirifera*.

27. A moxa stick as set forth in claim 26 in which said moxa consists of down separated from leaves of a species selected from the genus Artemisia.

28. A moxa stick as set forth in claim 21 in which said moxa consists of down separated from leaves of a species selected from the genus Artemisia.

29. A moxa stick as set forth in claim 6, in which said moxa consists of down separated from leaves of a species selected from the genus Aretemisia.

30. A moxa stick as set forth in claim 29, in which said species is selected from the group consisting of *Artemisia princeps Artemisia tridendata* and *Artemisia obsinthius*.

* * * * *